(12) United States Patent
Lee

(10) Patent No.: US 11,759,392 B2
(45) Date of Patent: Sep. 19, 2023

(54) AURICULAR ACUPUNCTURE PATCH TO WHICH ENERGY AND BLOOD STIMULATING PART IS ATTACHED

(71) Applicant: SEIGA INC., Daejeon (KR)

(72) Inventor: Kyung Tho Lee, Sejong (KR)

(73) Assignee: SEIGA INC., Daejeon (KR)

( * ) Notice: Subject to any disclaimer, the term of this patent is extended or adjusted under 35 U.S.C. 154(b) by 356 days.

(21) Appl. No.: 17/267,471

(22) PCT Filed: Aug. 20, 2019

(86) PCT No.: PCT/KR2019/010579
§ 371 (c)(1),
(2) Date: Feb. 9, 2021

(87) PCT Pub. No.: WO2020/045880
PCT Pub. Date: Mar. 5, 2020

(65) Prior Publication Data
US 2021/0290485 A1    Sep. 23, 2021

(30) Foreign Application Priority Data

Aug. 28, 2018  (KR) .................. 10-2018-0101195
Apr. 16, 2019  (KR) .................. 10-2019-0044257

(51) Int. Cl.
*A61H 39/04* (2006.01)
*A61H 39/08* (2006.01)
*A44C 7/00* (2006.01)

(52) U.S. Cl.
CPC ........... *A61H 39/04* (2013.01); *A61H 39/086* (2013.01); *A44C 7/00* (2013.01); *A61H 2201/10* (2013.01)

(58) Field of Classification Search
CPC ...... A61H 39/04; A61H 39/08; A61H 39/086; A61H 2205/027; A44C 7/00; A44C 7/002;
(Continued)

(56) References Cited

U.S. PATENT DOCUMENTS 8,761,872 B2 * 6/2014 Hinrichsen .......... A61H 39/002
607/2
2010/0241158 A1 * 9/2010 Hermon ................. A61H 39/08
606/204

(Continued)

FOREIGN PATENT DOCUMENTS

JP    2008-114009 A    5/2008
JP    3146315 U    11/2008
(Continued)

OTHER PUBLICATIONS

JP 3,146,315 (Jukichi), Nov. 13, 2008, Translation.*

*Primary Examiner* — Todd J Scherbel

(57) ABSTRACT

An auricular acupuncture patch to which an energy and blood stimulating part is attached is disclosed. The auricular acupuncture patch according to the present invention is attached along the reflect point of the ear, thereby being effective for treating dizziness, headaches, gastritis, asthma, gastroduodenal ulcers, enteritis, abdominal pain, diarrhea, bowel dysfunction, menstrual irregularity, insomnia, migraines, phobias, nervous vomiting, high fever, skin pruritus, oligogalactia, indigestion, obesity, smoking, and the like, and enabling the replacement of a decorative part, which are formed on the auricular acupuncture patch having the energy and blood stimulating part attached thereto, so as to provide various aesthetic effectiveness and conveniences in replacement.

1 Claim, 13 Drawing Sheets

(58) Field of Classification Search
CPC ......... A44C 7/004; A44C 7/007; A44C 7/008; A44C 7/009
See application file for complete search history.

(56) References Cited

U.S. PATENT DOCUMENTS

2011/0093049 A1* 4/2011 Hinrichsen ........ A61N 1/36017
607/72
2011/0137106 A1* 6/2011 Liang .................... A61N 2/002
600/15

FOREIGN PATENT DOCUMENTS

| JP | 2015-205155 A | 11/2015 |
|----|---------------|---------|
| KR | 20-0180161 Y1 | 4/2000 |
| KR | 20-0341583 Y1 | 9/2003 |
| KR | 20-2010-0010472 U | 10/2010 |

\* cited by examiner

AURICULAR ACUPUNCTURE PATCH TO WHICH ENERGY AND BLOOD STIMULATING PART IS ATTACHED

CROSS-REFERENCE TO PRIOR APPLICATIONS

This application is a national Stage Patent Application of PCT International Patent Application No. PCT/KR2019/010579, filed on Aug. 20, 2019 under 35 U.S.C. § 371, which claims priority of Korean Patent Application Nos. 10-2018-0101195, filed on Aug. 28, 2018 and 10-2019-0044257, filed on Apr. 16, 2019, which are all hereby incorporated by reference in their entirety.

TECHNICAL FIELD

The present invention relates to an auricular acupuncture patch having an energy and blood stimulating part attached thereto that is attached to the reflect point of the ear, thereby being effective for treating dizziness, headaches, gastritis, asthma, gastroduodenal ulcers, enteritis, abdominal pain, diarrhea, bowel dysfunction, menstrual irregularity, insomnia, migraines, phobias, nervous vomiting, high fever, skin pruritus, oligogalactia, indigestion, obesity, smoking, and the like.

Further, the present invention relates to an auricular acupuncture patch having an energy and blood stimulating part attached thereto that enables the replacement of a decorative part so as to provide various aesthetic effectiveness and conveniences in replacement.

BACKGROUND ART

Auricular acupuncture is used to find a specific point of the ear corresponding to a region of a body where a disease occurs and to then insert a needle into the specific point, thereby treating the disease. The auricular acupuncture is in line with the basic principle of oriental medicine through which good balance for the body is provided, but a method for performing the auricular acupuncture is easier than that in the oriental medicine.

Auricular acupuncture points are the acupuncture points of the ear corresponding to body regions where diseases occur, into which acupuncture is performed to heal the diseases. The auricular acupuncture points are called reflex points or healing points.

Up to now, 200 auricular acupuncture points have been known, and the number of auricular acupuncture points may increase according to studies in the future.

Generally, earrings are worn with magical meaning in ancient age, and they are worn with the meaning of jewel or shape thereof in present age. Otherwise, unique or functional earrings are selected to pursue both of uniqueness and beauty of a wearer.

In addition to the uniqueness and beauty, however, modern people also want to pursue their health, and accordingly, there is a need for development of a device having multiple functions capable of achieving all of them.

One of conventional technologies related to such a device is disclosed in Korean Utility Model Application No. 20-0341583. According to the conventional technology, an earring having medical wet strontium magnets built therein is worn according to the acupuncture points of the ear, thereby treating bad blood flow, muscle pain, obesity, headaches, shoulder pain, and so on.

FIG. 1 shows the conventional technology as mentioned above.

As shown in FIG. 1, an earring includes magnets 6 and 8 built in collets thereof in such a manner as to firmly engage with each other like teeth and to be thus seated onto the acupuncture points of the ear, and further, the front and back magnets 6 and 8 of the earring are different in size and are formed concavely 6' and convexly 8', so that they are inserted into the collets and come into close contact with the worn points (acupuncture points). Also, one (inner and back) collet is smaller than the other collet, which is because the skin surface of the ear is formed of a curve and a cartilage bone, unlike general skin surface, so that the earring looks more sophisticated and has enhanced contact force.

However, the conventional technology only provides indirect stimulation to the acupuncture points of the ear through the magnets, thereby making it difficult to expect a perfect treatment.

DISCLOSURE

Technical Problem

Accordingly, the present invention has been made in view of the above-mentioned problems occurring in the related art, and it is an object of the present invention to provide an auricular acupuncture patch that is provided with a stimulating part for applying direct stimulation to the reflex point of the ear.

It is another object of the present invention to provide an auricular acupuncture patch that is configured to have an energy and blood stimulating part cooperatively operating with a stimulating part to provide ear reflex reaction to the reflex point of the ear.

It is yet another object of the present invention to provide an auricular acupuncture patch that is capable of being detachably attached to the reflex point of the ear, with ease.

It is still another object of the present invention to provide an auricular acupuncture patch that is provided with a decorative part for uniqueness and beauty of women in such a manner as to be replaced easily with another decorative part with a desired design.

Technical Solution

To accomplish the above-mentioned objects, according to one aspect of the present invention, there is provided an auricular acupuncture patch including: a decorative part exposed to the outside when the auricular acupuncture patch is worn on the ear; an energy and blood stimulating part coupled to the decorative part to apply stimulation to the reflex point of the ear by means of energy generated therefrom; an attaching part coupled to the energy and blood stimulating part in such a manner as to allow a stimulating part to be fixedly attached to the reflex point of the ear; and the stimulating part coupled to the attaching part to apply direct physical stimulation to the reflex point of the ear.

To accomplish the above-mentioned objects, according to another aspect of the present invention, there is provided an auricular acupuncture patch including: a decorative part exposed to the outside when the auricular acupuncture patch is worn on the ear; a replaceable adhesive part whose one surface is attached to the decorative part and other surface is attached to an attaching part; the attaching part attached to the replaceable adhesive part in such a manner as to allow a stimulating part to be fixedly attached to the reflex point of the ear; and the stimulating part coupled to the attaching part to apply direct physical stimulation to the reflex point of the ear.

In this case, the auricular acupuncture patch further includes an energy and blood stimulating part located at a position where the decorative part is removed in such a manner as to be attached to top of the replaceable adhesive part to apply stimulation to the reflex point of the ear by means of a magnetic force generated therefrom.

Advantageous Effects

According to the present invention, the auricular acupuncture patch can directly apply physical stimulation to the ear and simultaneously apply magnetic flux line stimulation to the interior of the ear, thereby doubling the physical stimulation effectiveness.

In addition, the auricular acupuncture patch according to the present invention can easily replace the decorative part with another decorative part having a desired design, thereby providing various aesthetic effects.

EXPLANATIONS OF REFERENCE NUMERALS IN THE DRAWINGS

Figure 1:
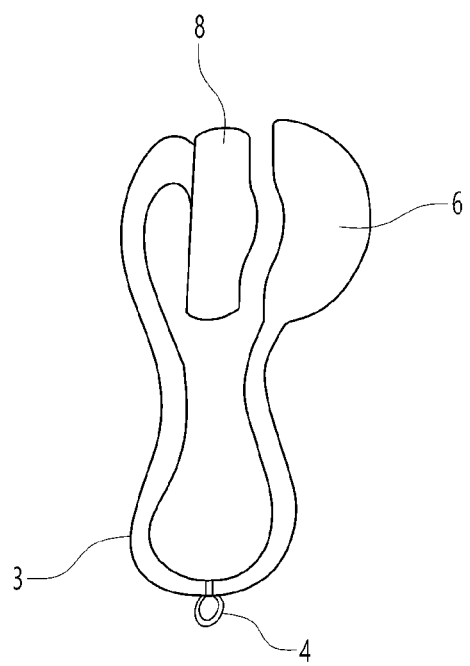
FIG. 1 is a perspective view showing a conventional technology.

100: decorative part
200: energy and blood stimulating part
300: attaching part
400: stimulating part
500: double face tape

BEST MODE FOR INVENTION

An auricular acupuncture patch according to a first embodiment of the present invention includes: a decorative part 100 exposed to the outside when the auricular acupuncture patch is worn on the ear; an energy and blood stimulating part 200 coupled to the decorative part 100 to apply energy stimulation to the reflex point of the ear by means of energy generated therefrom; an attaching part 300 coupled to the energy and blood stimulating part 200 in such a manner as to allow a stimulating part 400 to be fixedly attached to the reflex point of the ear; and the stimulating part 400 coupled to the attaching part 300 to apply direct physical stimulation to the reflex point of the ear.

Hereinafter, an explanation of the auricular acupuncture patch having the energy and blood stimulating part attached thereto according to the first embodiment of the present invention will be given in detail with reference to the attached drawings.

Figure 2:
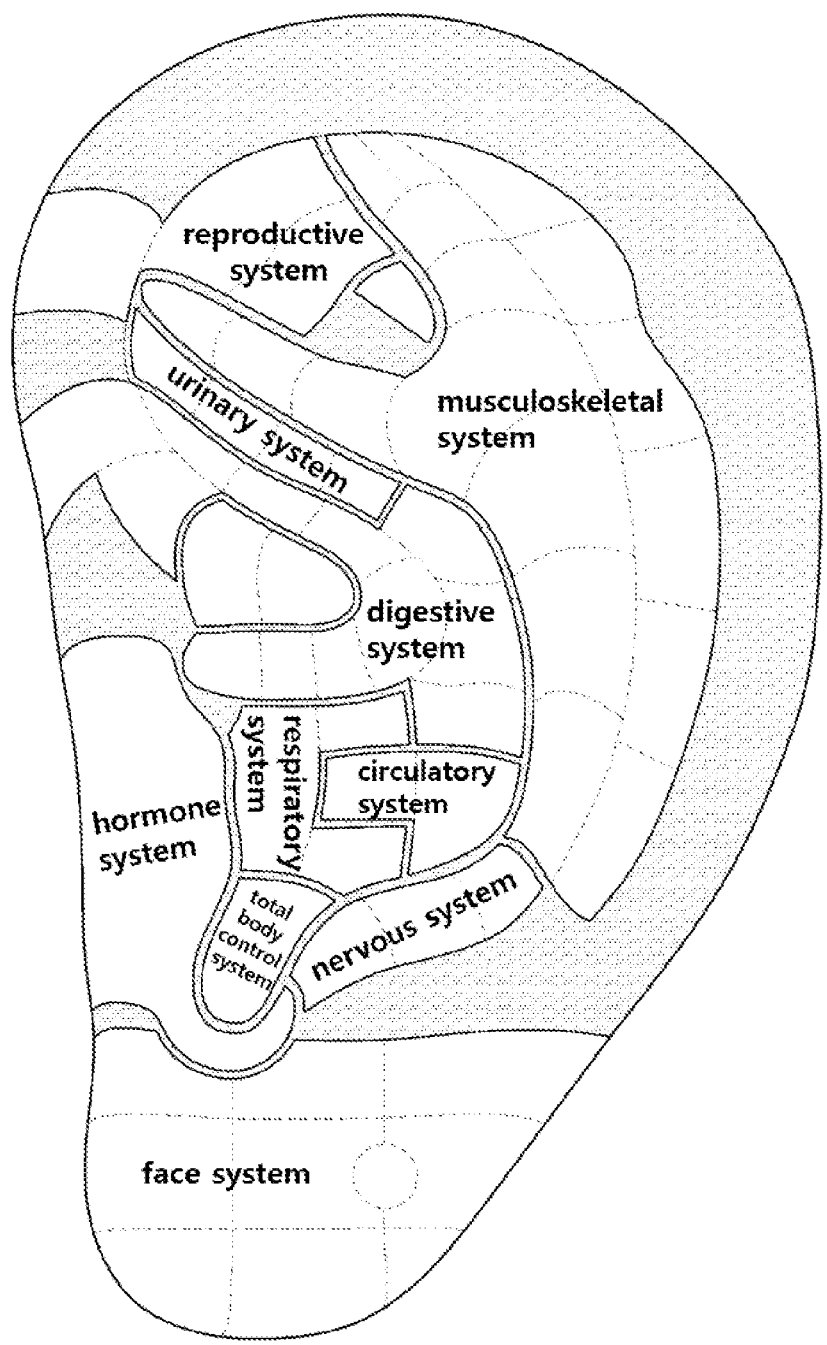
FIG. 2 is a diagram showing 10 systems on the reflex points of the ear.

FIG. 2 is a diagram showing 10 systems on the reflex points of the ear.

A plurality of reflex zones appearing on the ear of the human body are sortedly applied to the 10 systems as shown in FIG. 2 which are mentioned in human anatomy.

Systems defined generally in human anatomy indicate organs which cooperatively operate with one another to totally stabilize the human body and to achieve their common objects.

The 10 systems can be classified, based on anatomical names of the ear, into a face system, a hormone system, a total body control system, a nervous system, a respiratory system, a circulatory system, a digestive system, a urinary system, a reproductive system, and a musculoskeletal system.

The 10 systems are used to identify the reflex zones according to symptoms so that appropriate stimulation is applied to the identified reflex zones.

Figure 3:
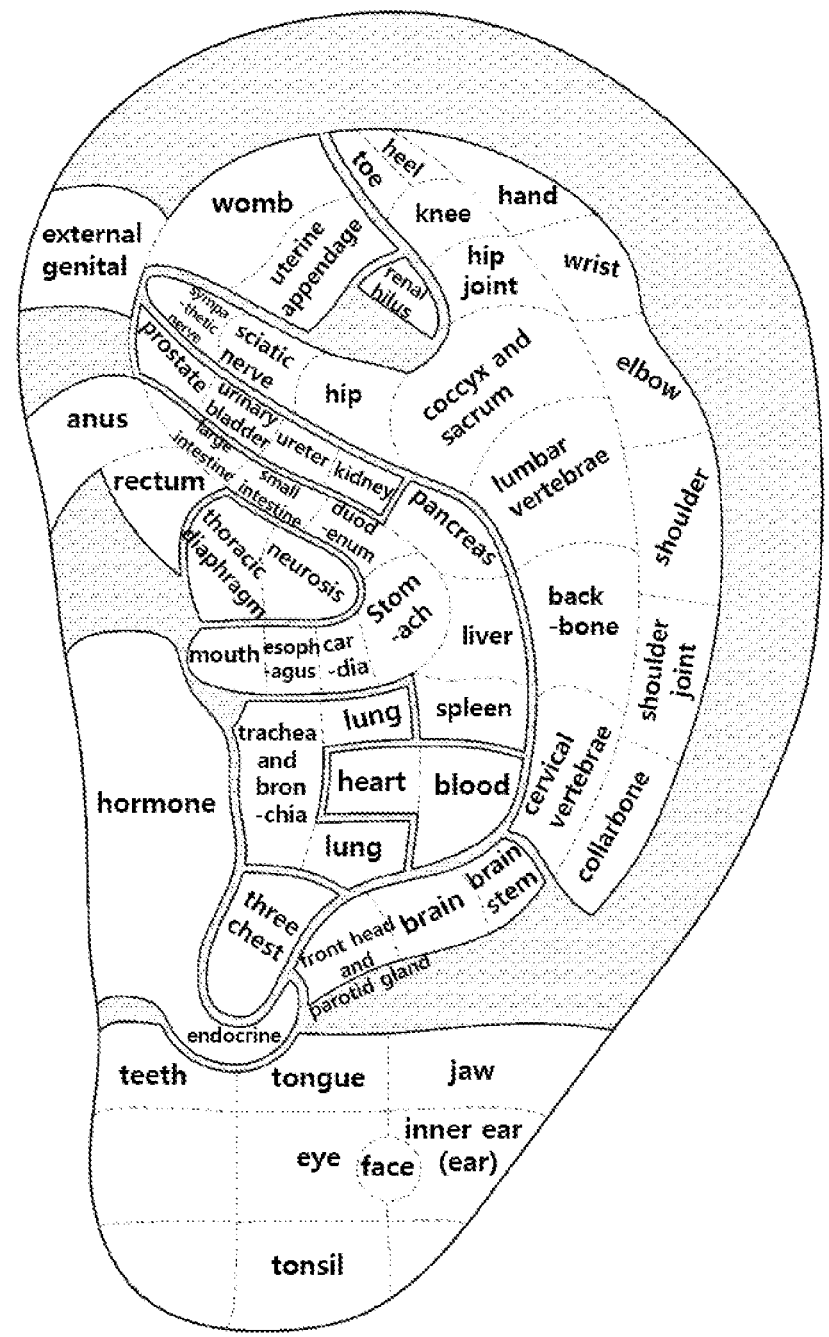
FIG. 3 is a diagram showing 59 reflex zones of the ear.

FIG. 3 is a diagram showing 59 reflex zones of the ear.

As shown in FIG. 3, the reflex zones (points), which indicate the same functions as one another or similar effectiveness to one another, are distributed on the ear, while forming given areas on the ear, and accordingly, they are sorted again according to their function.

The reflex zones (points) are specific areas (zones and points) in given rules on the surface of the ear, which correspond to the respective organs and tissues of the human body so as to reflect the physiology of the human body.

A method for selecting the reflex point or zone with respect to a given disease is divided into basic reflex zones, corresponding reflex zones, and reflex points.

If a given region of a body becomes abnormal, acupuncture points on the ear may be varied.

If the liver is not good, for example, a protrusion is formed from the region corresponding to the liver of the ear.

If the joint pain in knees is caused, further, a red blood vessel moves on the corresponding acupuncture point of the ear. Like this, if some changes (hyperemia, earwax, furuncle, color variation, protrusion, blood vessel, etc.) on the ear occur, they mean the body regions corresponding to the corresponding acupuncture points of the ear are not good.

The basic reflex zones are the reflex zones that correspond to the entire body to facilitate the metabolism of the body or the discharge of waste from the body and to keep the body healthy through an improvement in the circulation of blood and lymph.

Further, the basic reflex zones include the reflex zones commonly applied to sort diseases.

For example, in the case of a respiratory disease, the lung reflex zone, the trachea reflex zone, and the bronchia reflex zone are included in the basic reflex zones.

Accordingly, the basic reflex zones include a renal hilus reflex zone, a sympathetic reflex zone, an endocrine reflex zone, a subcortical reflex zone, and reflex zones commonly applied to respective diseases.

The corresponding reflex zones and the reflex points serve to reinforce the functions of the basic reflex zones, and most of them are connected to the organs with diseases.

If disease occurs on the body, variations may be formed on the reflex zone or reflex point of the ear corresponding to the region of the body where the disease occurs, and in specific, a change in color, a change in shape, a papule, a change in blood vessel, dead skin (skin keratin and dandruff), protrusion, and the like may occur as representative variations.

Most of the variations occur uniquely according to the reflex zones.

For example, the dead skin or protrusion appears on the subcortical reflex zone well, the change in color or dead skin appears on the reproductive organ reflex zone well, and the change in shape or hardening appears on the spinal reflex zone well.

If the variations which are not made on the normal ear occur on the ear, it is doubted that diseases or function abnormality occur on the organs corresponding to the reflex zones where the variations occur.

A method for keeping the ear healthy is classified into auricular acupuncture therapy and ear reflex therapy.

According to the present invention, the stimulating part serves as an auricular acupuncture needle, and the energy and blood stimulating part is used for the ear reflex therapy.

According to the present invention, the energy and blood stimulating part means a ball-shaped member made of germanium of 1 to 2 mm which is subjected to antibacterial and negative ion far infrared emission treatments, and otherwise, the energy and blood stimulating part means a magnet. The magnet is formed of a magnetic magnet or neodymium magnet (rare earth magnet). The energy and blood stimulating part functions as a tool for applying energy to a specific region of the human body through the application of far infrared rays or magnetic flux lines to thus allow the specific region to be treated through the reflex point of the human body.

TABLE 1

| Items | Auricular acupuncture | Energy and blood stimulating part |
| --- | --- | --- |
| Tools used | Needle, Stimulating part | Magnet, Germanium stone |
| Principle | Reflex acupuncture point | Reflex point |
| Stimulation strength | Strong | Gentle |
| Effectiveness keeping time | Kept effective after detachment | Kept effective at the time of attachment |
| Use conveniences | Difficult for ordinary person | Easy for ordinary person |
| Skill level | Advanced technique and experience | Easy in learning and use |
| Adverse effects | If occur, serious | Rare |
| Skin damage | Damage by needle | No |
| Cartilage destruction | Occurrable | Rare |
| Inflammation | Occurrable | Rare |
| Tool disinfection | Required (antibacterial treatment is possible) | Not required (antibacterial treatment is possible) |

Table 1 shows the comparison between the auricular acupuncture and the energy and blood stimulating part.

As appreciated from Table 1, the operations and effects of the auricular acupuncture are different from those of the energy and blood stimulating part.

If the far infrared rays or magnetic flux lines are applied to the region stimulated physically by the auricular acupuncture through the energy and blood stimulating part, the capillary vessels around the corresponding region are enlarged and the blood circulation is partially improved, so that the physical stimulation effectiveness through the auricular acupuncture can be doubly improved.

In addition to the physical stimulation on a specific acupuncture point only through the auricular acupuncture, that is, the heat effect around the corresponding region through the energy and blood stimulating part enables the physical stimulation effectiveness of the auricular acupuncture to be raised.

Figure 4:
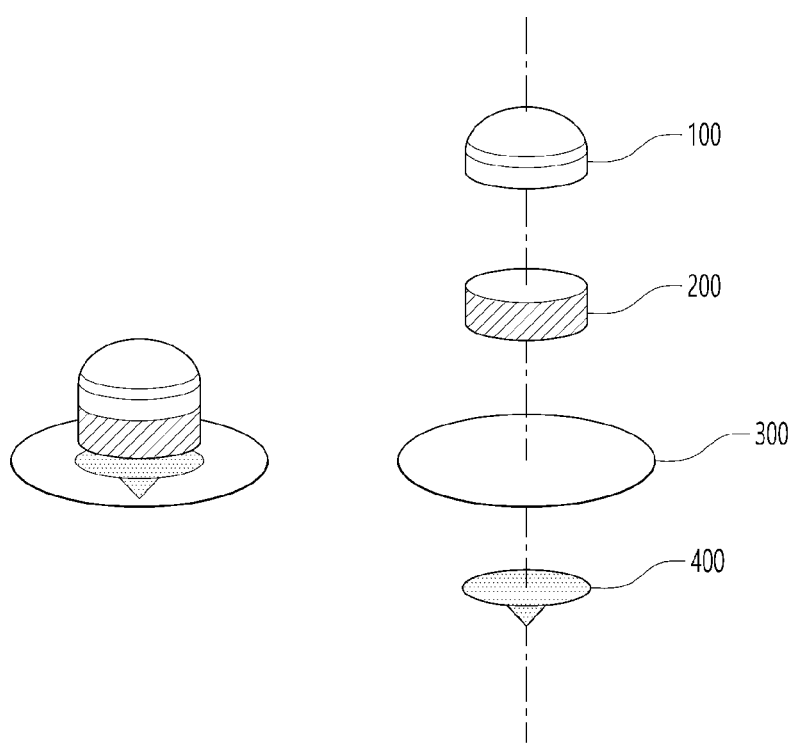
FIG. 4 is a perspective view showing an auricular acupuncture patch having an energy and blood stimulating part attached thereto according to a first embodiment of the present invention.

FIG. 4 is a perspective view showing an auricular acupuncture patch having an energy and blood stimulating part attached thereto according to a first embodiment of the present invention.

Referring to FIG. 4, an auricular acupuncture patch according to a first embodiment of the present invention has a decorative part 100 located on top thereof and made of jewel like crystal, pearl, and so on. Otherwise, the decorative part 100 may be made of cubic zirconia, metal, ceramic, and so on. The decorative part 100 is a member that provides beauty and uniqueness for a woman, so that she has no reluctance in wearing the auricular acupuncture patch.

An energy and blood stimulating part 200 is located on the underside of the decorative part 100 and is made of a magnet or germanium. If the energy and blood stimulating part 200 is made of the magnet, desirably, it is located to have the N pole with respect to a skin direction to allow flows of energy and blood to be better. The strength of the magnet is desirably in the range of 2000 to 2500 Gauss, which has the greatest influence on the flow of blood and provides the smallest adverse effects.

The energy and blood stimulating part 200 has an influence on the flow of blood and provides energy through the reflex point. The energy and blood stimulating part 200 is desirably made of the ball-shaped germanium stone of 1 to 2 mm which is subjected to anti-bacterial and negative ion far infrared emission treatments.

An attaching part 300 is located on the underside of the energy and blood stimulating part 200 and serves as an adhesive for attaching the auricular acupuncture patch onto the ear. The energy and blood stimulating part 200 and the attaching part 300 may be attached to each other by means of a double face tape 500.

The attaching part 300 looks good on the decorative part 100 so that it can be seen like an earring to the outside.

The attaching part 300 is called 'patch', which is different from the double face tape 500. The patch is made of a tape whose one surface is attachable, and in some cases, it may be replaced with a functional patch attached to the ear. In the case of a person who has motion sickness, for example, the attaching part 300 may be replaced with a motion sickness prevention patch.

Further, various medicines may be mixed with the adhesive to optimize the effectiveness of the auricular acupuncture patch.

The medicines include chemicals and biochemicals such as scopolamine, belladonna extract, scopolia japonica, and so on.

A stimulating part 400 is located on the underside of the patch (attaching part) 300 and has a top having a smaller area than the attaching part 300. Accordingly, the attaching part 300 accommodates the stimulating part 400 therein to allow the stimulating part 400 to be seated onto the ear.

The stimulating part 400 is called a pressure bar, a pressure needle, or a tip. The stimulating part 400 is made of metal, resin, wood, ceramic, or the like, and if the stimulating part 400 is made of metal, the metal is subjected to a gold or silver plating treatment so as to prevent an allergic reaction to the metal.

If the stimulating part 400 is made of a magnetic material and the energy and blood stimulating part 200 is made of a magnet, particularly, the stimulating part 400 is connected to the magnet to make the magnetic force stronger.

Accordingly, the stimulation applied to the reflex point can be stronger than before.

The stimulating part 400 is excellent in releasing the acupuncture point.

According to the present invention, the auricular acupuncture patch is used together with the energy and blood stimulating part 200, as suggested in Table 1, so that in this case, the effectiveness is more raised than that expected when the auricular acupuncture patch is used separately from the energy and blood stimulating part 200.

In specific, the acupuncture point can be released by means of the stimulating part 400, and the flow of blood can be improved by means of the energy and blood stimulating part 200. Accordingly, the acupuncture point blocked is released (through the stimulating part 400), and before the effectiveness disappears, simultaneously, the flow of blood is improved (through the energy and blood stimulating part 200), thereby doubling the effectiveness.

Figure 5:
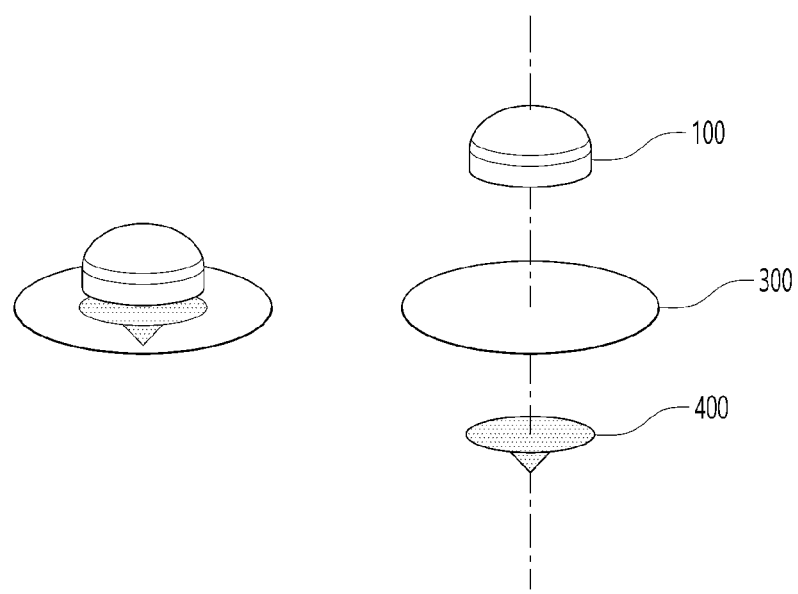
FIG. 5 is a perspective view showing a variation of the auricular acupuncture patch of FIG. 4.

FIG. 5 is a perspective view showing a variation of the auricular acupuncture patch of FIG. 4.

As shown in FIG. 5, an auricular acupuncture patch according to a variation of the present invention includes: a decorative part 100 exposed to the outside when the auricular acupuncture patch is worn on the ear; an attaching part 300 coupled to the decorative part 100 in such a manner as to allow a stimulating part 400 to be fixedly attached to the reflex point of the ear;

and the stimulating part 400 coupled to the attaching part 300 to apply direct physical stimulation to the reflex point of the ear.

In specific, the energy and blood stimulating part 200 is not located in the first variation of the present invention, thereby having no best effectiveness, but advantageously, the effectiveness of the auricular acupuncture can be easily obtained, while the beauty of the earring is being improved.

Figure 6:
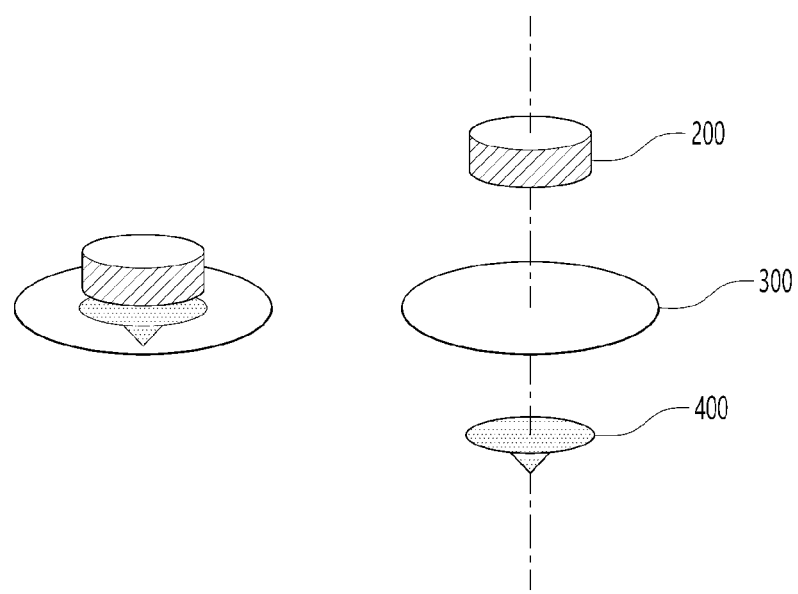
FIG. 6 is a perspective view showing another variation of the auricular acupuncture patch of FIG. 4.

FIG. 6 is a perspective view showing another variation of the auricular acupuncture patch of FIG. 4.

As shown in FIG. 6, an auricular acupuncture patch according to another variation of the present invention includes: an energy and blood stimulating part 200 for applying stimulation to the reflex point of the ear by means of energy generated therefrom; an attaching part 300 coupled to the energy and blood stimulating part 200 in such a manner as to allow a stimulating part 400 to be fixedly attached to the reflex point of the ear; and the stimulating part 400 coupled to the attaching part 300 to apply direct physical stimulation to the reflex point of the ear.

In specific, the energy and blood stimulating part 200, the attaching part 300, and the stimulating part 400 are provided in another variation of the present invention, without any decorative part 100, so that the auricular acupuncture patch can be used for men. In this case, the energy and blood stimulating part 200 and the attaching part 300 have skin colors so that the auricular acupuncture patch worn on the ear cannot be recognized to the outside.

Figure 7:
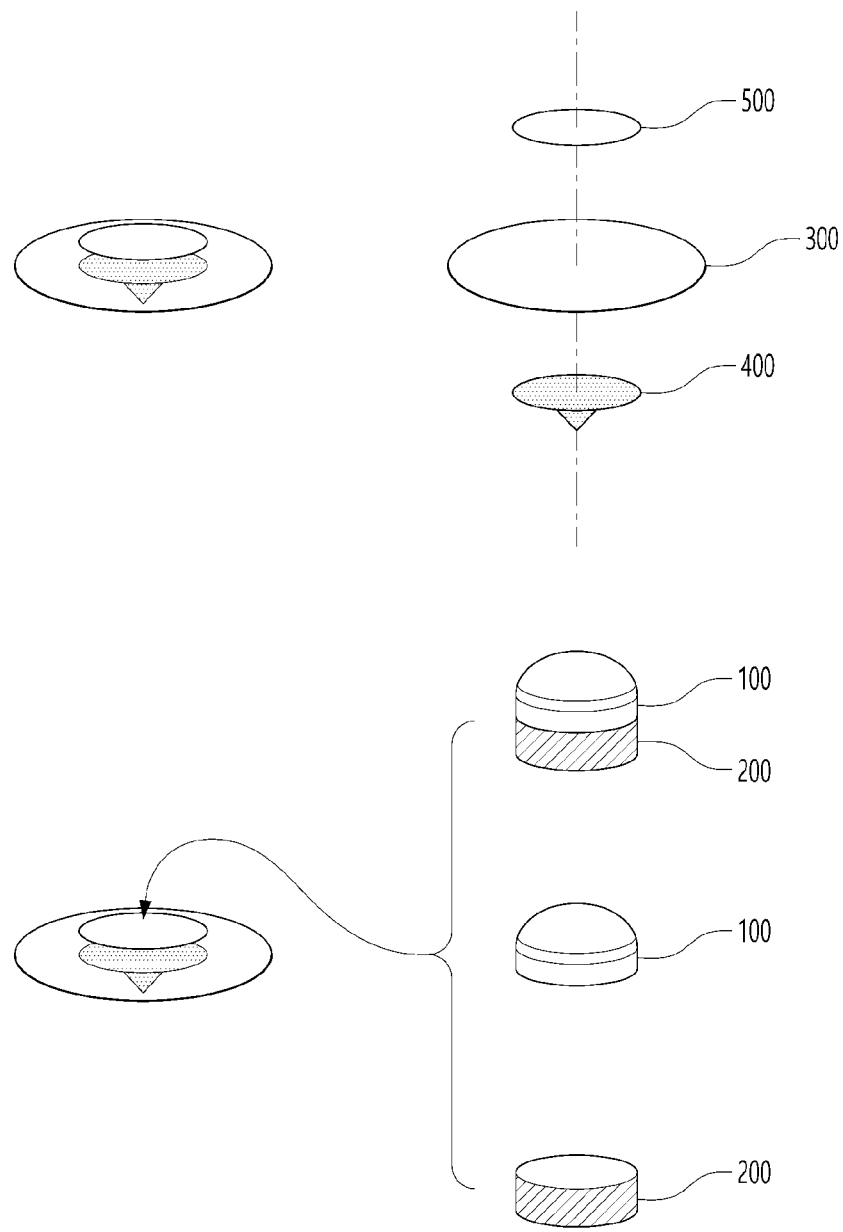
FIG. 7 is a perspective view showing yet another variation of the auricular acupuncture patch of FIG. 4.

FIG. 7 is a perspective view showing yet another variation of the auricular acupuncture patch of FIG. 4.

As shown in FIG. 7, an assembly which is made by attaching the decorative part and the energy and blood stimulating part to each other is separately made and sold as one product, so that it can be purchased and coupled to the attaching part according to a user's preference.

MODE FOR INVENTION

Hereinafter, an explanation of the auricular acupuncture patch having the energy and blood stimulating part attached thereto according to a second embodiment of the present invention will be given in detail with reference to FIGS. 8 to 13.

A decorative part applied to the second embodiment of the present invention is more easily replaced when compared with that applied to the first embodiment of the present invention.

An auricular acupuncture patch according to the second embodiment of the present invention includes: a decorative part 100 exposed to the outside when the auricular acupuncture patch is worn on the ear; a replaceable adhesive part 150 whose one surface is attached to the decorative part 100 and other surface is attached to an attaching part 300; the attaching part 300 attached to the replaceable adhesive part 150 in such a manner as to allow a stimulating part 400 to be fixedly attached to the reflex point of the ear; and the stimulating part 400 coupled to the attaching part 300 to apply direct physical stimulation to the reflex point of the ear.

In this case, the decorative part 100 may be replaced with an energy and blood stimulating part 200 for applying stimulation to the reflex point of the ear by means of a magnetic force generated therefrom, and the energy and blood stimulating part 200 is attached to the replaceable adhesive part 150.

Figure 8:
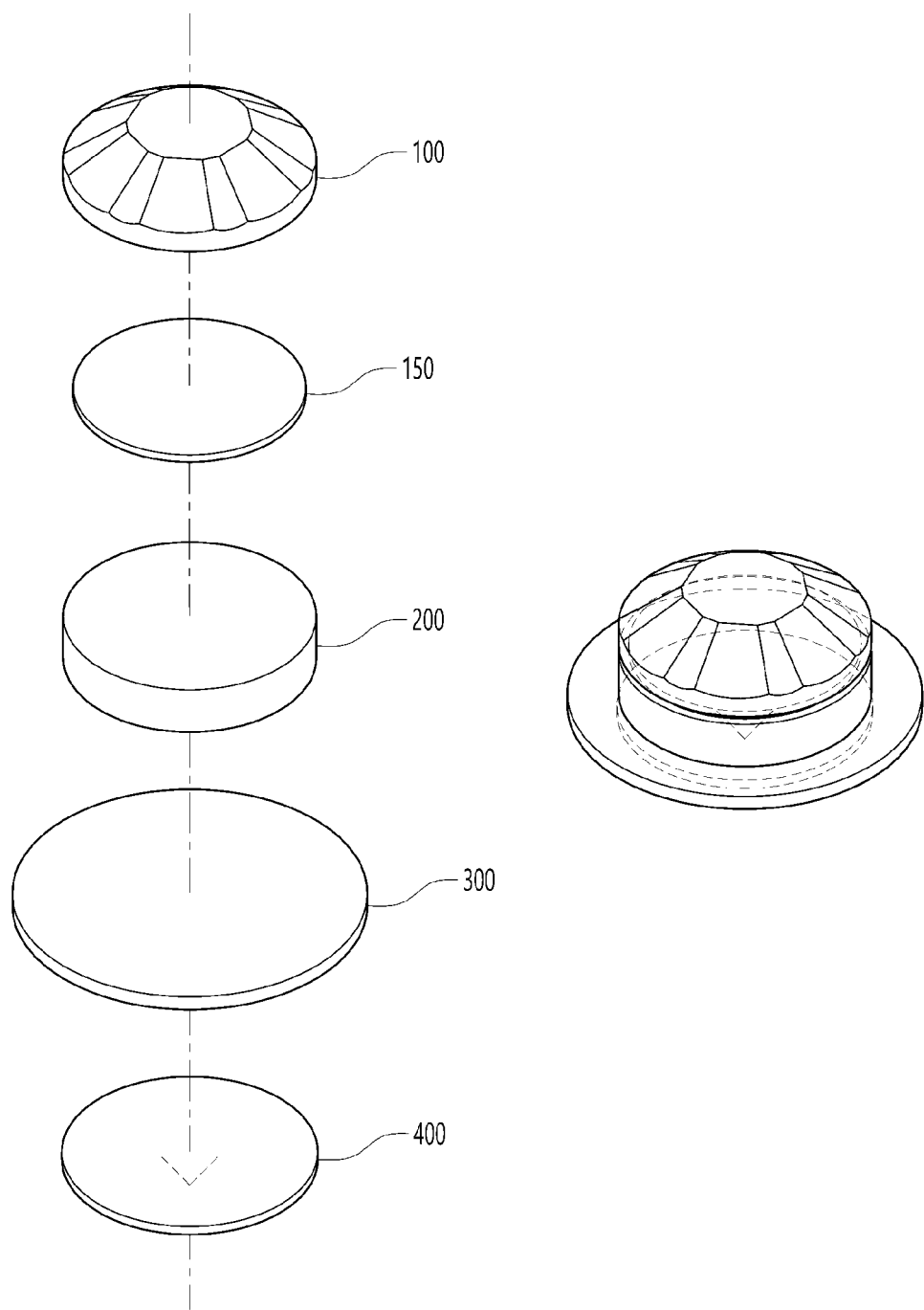
FIG. 8 is a perspective view showing an auricular acupuncture patch having an energy and blood stimulating part attached thereto according to a second embodiment of the present invention.

FIG. 8 is a perspective view showing the auricular acupuncture patch according to the second embodiment of the present invention.

Referring to FIG. 8, the auricular acupuncture patch according to the second embodiment of the present invention has the decorative part 100 located on top thereof and made of jewel like crystal, pearl, and so on. Otherwise, the decorative part 100 may be made of cubic zirconia, metal, ceramic, and so on. The decorative part 100 is a member that provides beauty and uniqueness for a woman, so that she has no reluctance in wearing the auricular acupuncture patch.

However, the decorative part 100 has only one jewel attached thereto, and even if the wearer wants to replace the current jewel with another jewel, the decorative part 100 cannot be exchanged with new one, thereby undesirably purchasing a new auricular acupuncture patch. So as to solve such a problem, the decorative part 100 can be replaced with another decorative part periodically or if necessary.

In specific, one surface of the replaceable adhesive part 150 is attached to the decorative part 100, and the other surface is attached to the attaching part 300.

According to an additional aspect of the present invention, the decorative part 100 and the replaceable adhesive part 150 as a group are fixedly attached to the attaching part 300. That is, the decorative part 100 can be replaced with another decorative part the user wants to have.

The decorative part 100 as mentioned in the present invention is jewel or an energy and blood stimulating part, and the decorative part 100 means any one of the jewel and the energy and blood stimulating part as mentioned in the present invention.

According to another additional aspect of the present invention, on the other hand, the auricular acupuncture patch according to the second embodiment of the present invention further includes an energy and blood stimulating part 200 coupled to the decorative part 100 to apply stimulation to the reflex point of the ear by means of a magnetic force generated therefrom.

In this case, the energy and blood stimulating part 200 is located on the underside of the replaceable adhesive part 150.

Figure 9:
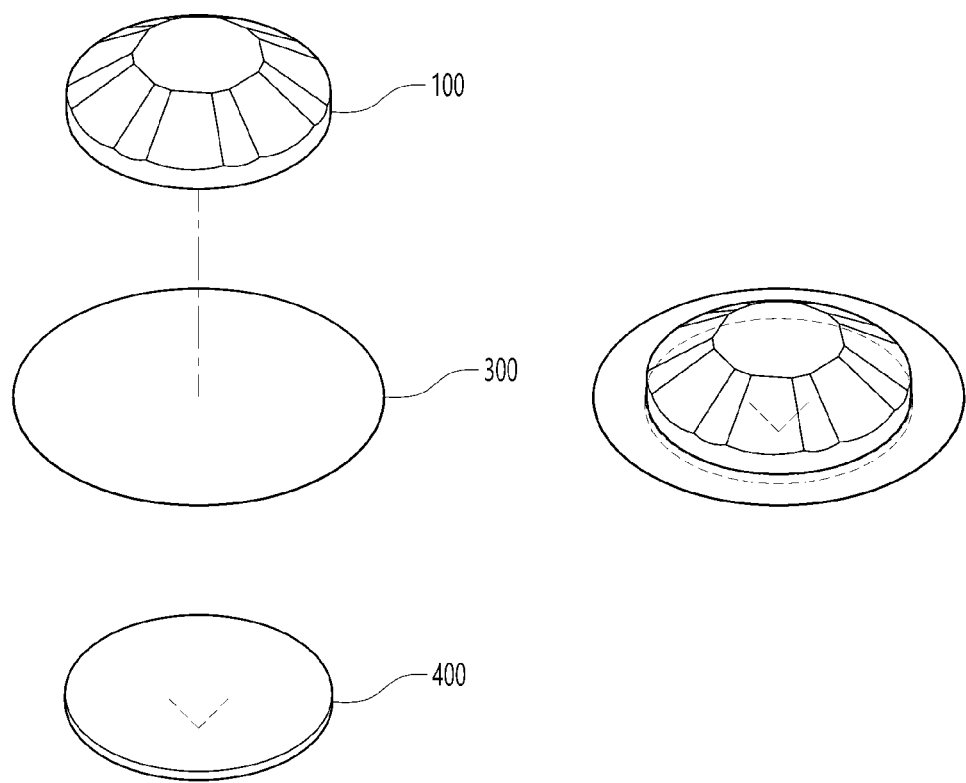
FIG. 9 is a perspective view showing a variation of the auricular acupuncture patch of FIG. 8.

FIG. 9 is a perspective view showing a variation of the auricular acupuncture patch of FIG. 8.

As shown in FIG. 9, an auricular acupuncture patch includes:

a decorative part 100 exposed to the outside when the auricular acupuncture patch is worn on the ear; an attaching part 300 coupled to the decorative part 100 in such a manner as to allow a stimulating part 400 to be fixedly attached to the reflex point of the ear; and the stimulating part 400 coupled to the attaching part 300 to apply direct physical stimulation to the reflex point of the ear.

In specific, the energy and blood stimulating part 200 is not located therein, thereby having no best effectiveness, but advantageously, the effectiveness of the auricular acupuncture can be easily obtained, while the beauty of the earring is being improved.

Further, adhesive layers are formed on both surfaces of the attaching part so that the decorative part 100 is located on top adhesive layer and the stimulating part 400 on underside adhesive layer.

In this case, only the decorative part attached to top adhesive layer is replaced with desired jewel.

Figure 10:
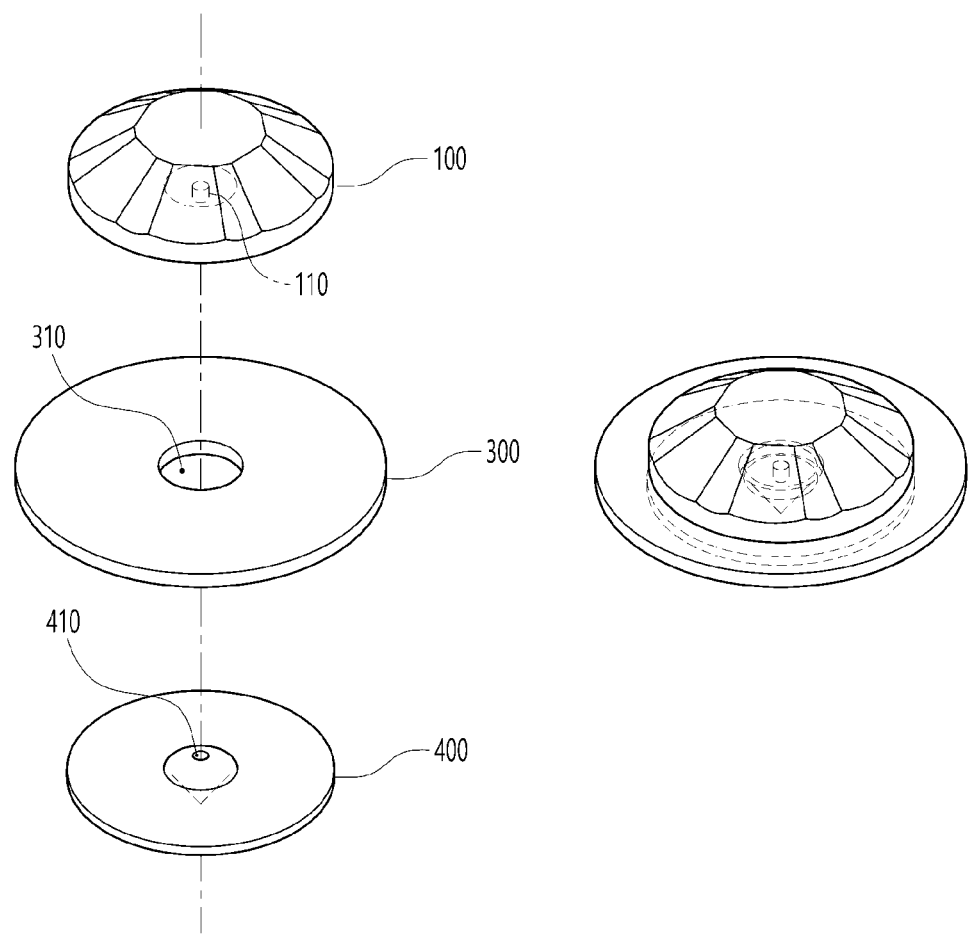
FIG. 10 is a perspective view showing another variation of the auricular acupuncture patch of FIG. 8.

FIG. 10 is a perspective view showing another variation of the auricular acupuncture patch of FIG. 8.

As shown in FIG. 10, an auricular acupuncture patch includes: a decorative part 100 exposed to the outside when the auricular acupuncture patch is worn on the ear; a protrusion 110 protruding downward by a given distance from the decorative part 100; an attaching part 300 having a hole 310 formed at a position corresponding to the protrusion 110 in such a manner as to allow a stimulating part 400 to be fixedly attached to the reflex point of the ear; and the stimulating part 400 coupled to the attaching part 300, having a concave portion 410 formed thereon with a given distance to detachably insert the protrusion 110, and applying direct physical stimulation to the reflex point of the ear.

Under the above configuration, the protrusion 110 is extended from the underside of the decorative part 100, and the concave portion 410 is formed on the stimulating part 400.

In this case, the hole 310 is formed on the attaching part 300 to allow the protrusion 110 to be coupled to the concave portion 410.

If the decorative part 100 is separated from the stimulating part 400, accordingly, the protrusion 110 escapes from the concave portion 410, so that the decorative part 100 can be easily replaced with another decorative part.

For example, a snap structure is provided so that the decorative part 100 can be detachably attached to the stimulating part 400 easily by means of the wearer.

According to one aspect of the present invention, the energy and blood stimulating part 200 may be located between the decorative part 100 and the attaching part 300.

Figure 11:
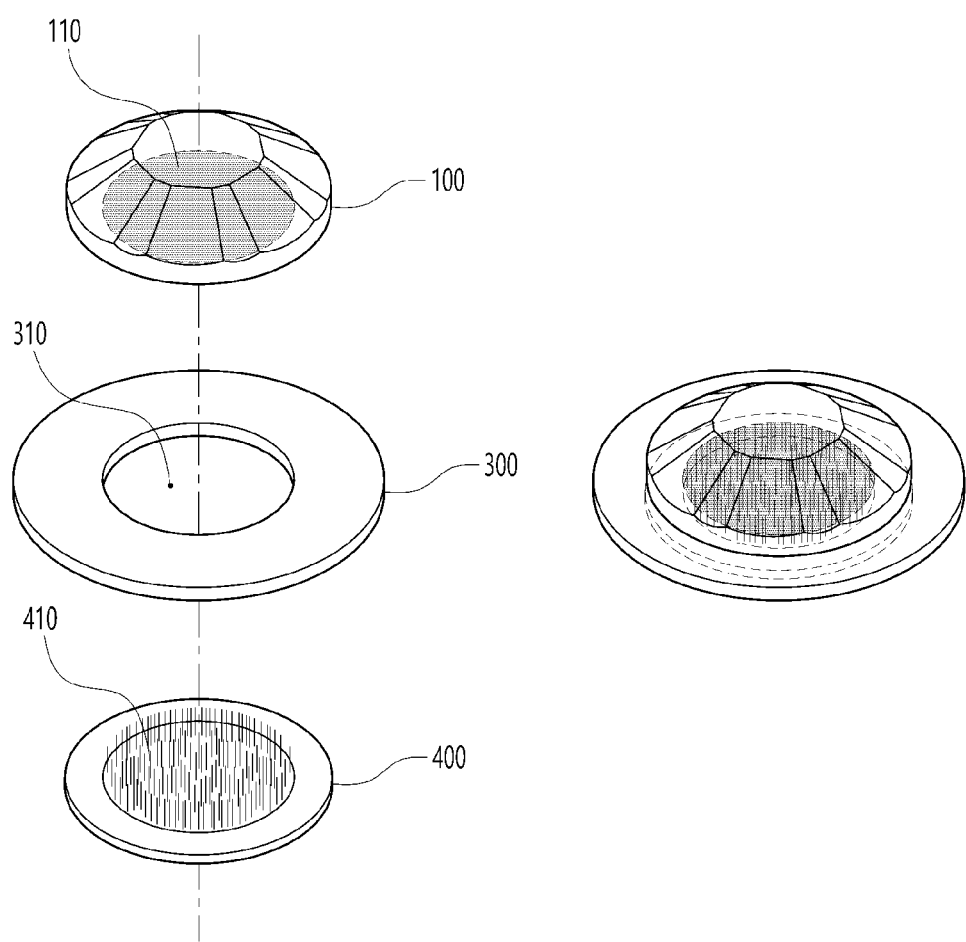
FIG. 11 is a perspective view showing yet another variation of the auricular acupuncture patch of FIG. 8.

FIG. 11 is a perspective view showing yet another variation of the auricular acupuncture patch of FIG. 8.

As shown in FIG. 11, an auricular acupuncture patch includes: a decorative part 100 exposed to the outside when the auricular acupuncture patch is worn on the ear; a first Velcro part 110 located on the underside of the decorative part 100; an attaching part 300 having a hole 310 formed at a position corresponding to the protrusion 110 in such a manner as to allow a stimulating part 400 to be fixedly attached to the reflex point of the ear; and the stimulating part 400 coupled to the attaching part 300, having a second Velcro part 410 located thereon, to which the first Velcro part 110 is detachably attached, and applying direct physical stimulation to the reflex point of the ear.

Under the above configuration, the first Velcro part 110 is located on the underside of the decorative part 100, and the second Velcro part 410 is located on the stimulating part 400 to correspond to the first Velcro part 110, so that the first Velcro part 110 and the second Velcro part 410 are attached to each other.

If the first Velcro part 110 is separated from the second Velcro part 410, accordingly, the decorative part 100 is separated from the stimulating part 400.

The various variations of the auricular acupuncture patch according to the first and second embodiments of the present invention have been described above.

Figures 12A, 12B:
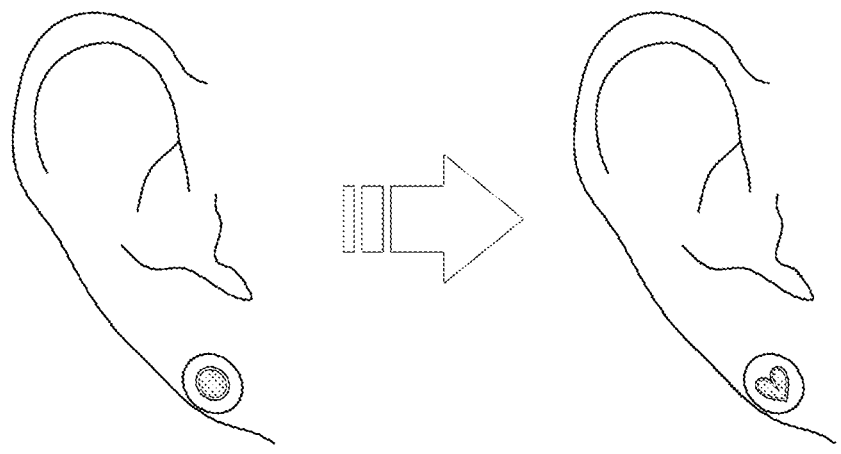
FIGS. 12A and 12B are perspective views showing a replacing process of the decorative part according to the present invention.

For example, as shown in FIGS. 12A and 12B, circular cubic zirconia is used for the auricular acupuncture patch, and it may be replaced with heart-shaped jewel if needed.

Further, an assembly which is made by attaching the decorative part and the energy and blood stimulating part to each other is separately made and sold as one product, so that it can be purchased and coupled to the attaching part according to a user's preference.

Figure 13:
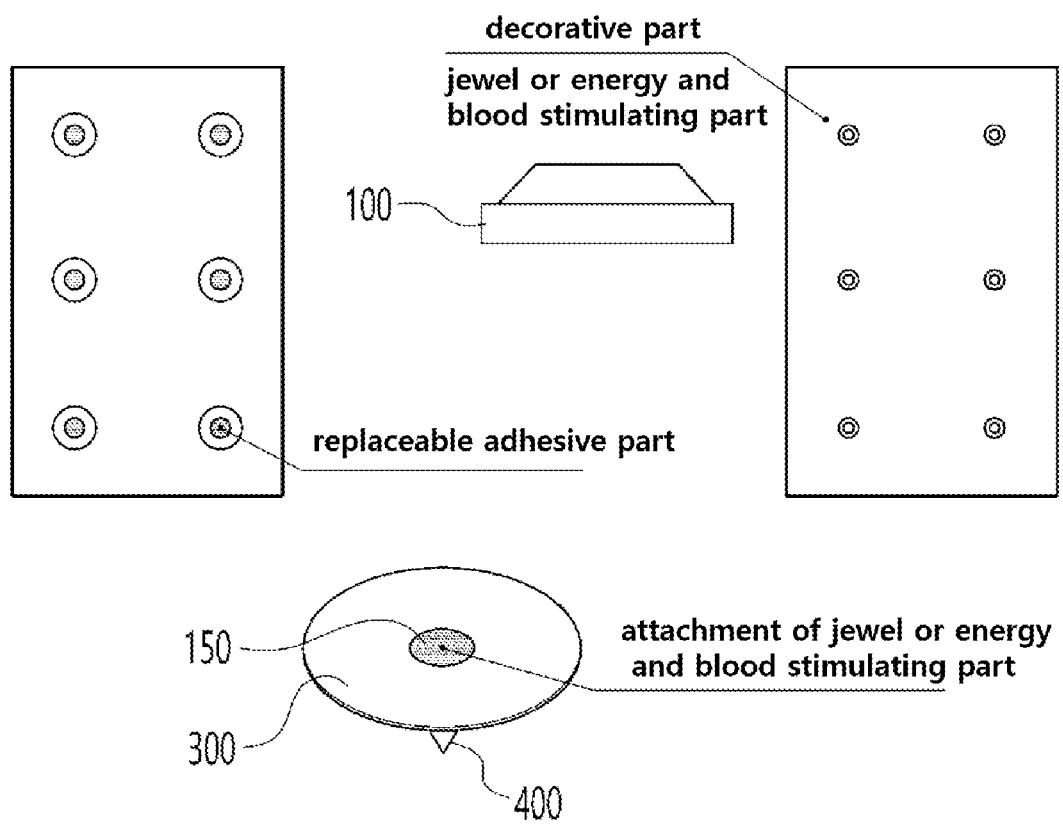
FIG. 13 is a view showing still another variation of the auricular acupuncture patch of FIG. 8.

FIG. 13 is a view showing still another variation of the auricular acupuncture patch of FIG. 8.

An auricular acupuncture patch according to the variation of the present invention includes: a decorative part 100 exposed to the outside when the auricular acupuncture patch is worn on the ear; a replaceable adhesive part 150 whose one surface is attached to the decorative part 100 and other surface is attached to an attaching part 300; the attaching part 300 attached to the replaceable adhesive part 150 in such a manner as to allow a stimulating part 400 to be fixedly attached to the reflex point of the ear; and the stimulating part 400 coupled to the attaching part 300 to apply direct physical stimulation to the reflex point of the ear.

For example, a first sheet having a plurality of jewel-like decorative parts or energy and blood stimulating parts with various shapes (star, circle, square, triangle, and so on), colors (red, blue, yellow, green, and so on), and functions (in the case of the energy and blood stimulating part, functions as neodymium magnet, germanium magnet, and so on) is provided as one product, and further, a second sheet having a plurality of sets each having one replaceable adhesive part, one attaching part, and one stimulating part is provided as one product. Accordingly, the wearer's desired jewel is selected from the first sheet and is coupledly attached to one set on the second sheet.

According to an additional aspect of the present invention, further, the decorative part 100 may be replaced with the energy and blood stimulating part 200 for applying stimulation to the reflex point of the ear by means of a magnetic force generated therefrom, and next, the energy and blood stimulating part 200 is attached to top of the replaceable adhesive part 150.

Instead of the decorative parts, that is, the plurality of energy and blood stimulating parts may be provided on the first sheet.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. An auricular acupuncture patch comprising:
   a decorative part exposed to outside when the auricular acupuncture patch is worn on the ear;
   a replaceable adhesive part comprising a first side and a second side opposite the first side, wherein the first side is adhered to the decorative part,
   an energy and blood stimulating part generating a magnetic force, the energy and blood stimulating part adhered to the second side of the replaceable adhesive part wherein the energy and blood stimulating part is configured to apply stimulation to the reflex point of the ear by means of the magnetic force;
   an attaching part comprising a third side and a fourth side opposite the third side, the attaching part coupled to the energy and blood stimulating part on the third side; and
   a stimulating part coupled to the attaching part on the fourth side, wherein:
   the stimulating part is configured to be fixedly attached to the reflex point of the ear to apply direct physical stimulation to the reflex point of the ear;
   the third side of the attaching part, which interfaces with the energy and blood stimulating part, has a first surface area larger than a second surface area of a surface, of the energy and blood stimulating part, which interfaces with the attaching part;
   the energy and blood stimulating part is prevented from contacting the reflex point of the ear by the attaching part, when the auricular acupuncture patch is worn on the ear; and
   the decorative part is replaceable with the replaceable adhesive part.

* * * * *